United States Patent
Ryu et al.

(10) Patent No.: US 6,805,780 B1
(45) Date of Patent: Oct. 19, 2004

(54) ELECTROCHEMICAL BIOSENSOR TEST STRIP, FABRICATION METHOD THEREOF AND ELECTROCHEMICAL BIOSENSOR

(75) Inventors: Junoh Ryu, Seoul (KR); Jinwoo Lee, Gyenggi-do (KR)

(73) Assignee: Allmedicus Co., Ltd., Gyunggi-do (KR)

( * ) Notice: Subject to any disclaimer, the term of this patent is extended or adjusted under 35 U.S.C. 154(b) by 0 days.

(21) Appl. No.: 09/958,259

(22) PCT Filed: Apr. 6, 2000

(86) PCT No.: PCT/KR00/00313
§ 371 (c)(1),
(2), (4) Date: Oct. 5, 2001

(87) PCT Pub. No.: WO00/60340
PCT Pub. Date: Oct. 12, 2000

(30) Foreign Application Priority Data

Apr. 6, 1999 (KR) ............................. 1999-11810
Oct. 29, 1999 (KR) ............................. 1999-47573

(51) Int. Cl.⁷ ............................................ G01N 27/327
(52) U.S. Cl. ..................... 204/403.01; 204/403.14; 204/409; 204/192.2
(58) Field of Search ............. 204/403.01, 403.14, 204/409, 192.2

(56) References Cited

U.S. PATENT DOCUMENTS 4,615,781 A * 10/1986 Boudreau ............. 204/192.15
5,120,420 A   6/1992 Nankai et al.
5,194,133 A * 3/1993 Clark et al. ................. 204/608
5,264,103 A * 11/1993 Yoshioka et al. ........... 205/778
5,346,601 A * 9/1994 Barada et al. ......... 204/192.15
5,437,999 A   8/1995 Diebold et al.
5,567,302 A * 10/1996 Song et al. ............... 205/777.5
5,762,770 A   6/1998 Pritchard et al.
6,146,489 A * 11/2000 Wirth ........................ 156/280
6,469,439 B2 * 10/2002 Himeshima et al. ........ 313/506

FOREIGN PATENT DOCUMENTS

| JP | 7-325064 | 12/1995 |
| JP | 10-318970 | 12/1998 |
| KR | 97-2305 | 1/1997 |
| KR | 97-66561 | 10/1997 |

* cited by examiner

Primary Examiner—Kaj K. Olsen
(74) Attorney, Agent, or Firm—Timothy J. Keefer; Seyfarth Shaw LLP

(57) ABSTRACT

Electrochemical biosensor test strip, fabrication method thereof and electrochemical biosensor are disclosed. The electrochemical biosensor test strip is fabricated by cutting a groove in a first insulation base in the breadth direction, forming two electrodes parallel to length direction on the first insulation base by sputtering using shadow mask, fixing a reaction material comprising an enzyme which reacts an analyte and generates current corresponding to the concentration of analyte across the two electrodes on the groove of the insulation base, and affixing a cover to the first insulation base. The groove of the first insulation base and the cover make a capillary at the position where the reaction material is fixed. The fabrication method can lower the cost for fabricating the test strip by forming thin electrodes.

16 Claims, 8 Drawing Sheets

ELECTROCHEMICAL BIOSENSOR TEST STRIP, FABRICATION METHOD THEREOF AND ELECTROCHEMICAL BIOSENSOR

CROSS REFERENCE TO RELATED APPLICATION

This application claims the priority of Korean patent application Ser. No. 1999-11810 filed on Apr. 6, 1999 and Korean patent application Ser. No. 1999-47573 filed on Oct. 29, 1999.

TECHNICAL FIELD

The present invention relates to an electrochemical biosensor test strip for quantitative analysis of analytes of interest, a method for fabricating the same, and an electrochemical biosensor using the same.

BACKGROUND

In the medical field, electrochemical biosensors are extensively used to analyze biomaterials, including blood. Of them, enzyme-utilizing electrochemical biosensors are most predominant in hospital or clinical laboratories because they are easy to apply and superior in measurement sensitivity, allowing the rapid acquisition of test results. For electrochemical biosensors, electrode methods have recently been extensively applied. For example, in an electrode system established by screen printing, the quantitative measurement of an analyte of interest can be achieved by fixing a reagent comprising an enzyme onto the electrodes, introducing a sample, and applying an electric potential across the electrodes.

An electrochemical biosensor using such an electrode method may be referred to U.S. Pat. No. 5,120,420, which discloses an electrochemical biosensor test strip taking advantage of a capillary space for the introduction of analytes, teaching the use of a spacer between an insulating substrate and a cover to form the capillary space.

Another electrochemical biosensor test strip can be found in U.S. Pat. No. 5,437,999, in which a patterning technique, typically used in the PCB industry, is newly applied for the fabrication of an electrochemical biosensor, leading to an achievement of precisely defined electrode areas. This electrochemical biosensor test strip is allegedly able to precisely determine analyte concentrations on a very small sample size.

With reference to FIG. 1, there is an opposing electrode type of an electrochemical biosensor test strip described in U.S. Pat. No. 5,437,999, specified by a disassembled state in an exploded perspective view of FIG. 1A and by an assembled state in a perspective view of FIG. 1B. Typically, these sensors perform an electrochemical measurement by applying a potential difference across two or more electrodes which are in contact with a reagent and sample. As seen in the figure, the electrochemical biosensor test strip comprises two electrodes: a working electrode on which reactions occur and a reference electrode which serves as a standard potential.

There are two ways of arranging such working and reference electrodes. One is of an opposing electrode type just like that shown in FIG. 1A, in which a working electrode formed substrate is separated from a reference electrode by a spacer in a sandwich fashion. The other is of an adjacent type in which a working and a reference electrode both are fabricated on the same substrate side-by-side in a parallel fashion. U.S. Pat. No. 5,437,999 also discloses an adjacent electrode electrochemical biosensor, adopting a spacer that separates an insulating substrate, on which the electrodes are fabricated, from another insulating substrate, which serves as a cover, forming a capillary space.

In detail referring to FIG. 1, a reference electrode-formed substrate, that is, a reference electrode element 10, is spatially separated from a working electrode-formed substrate, that is a working electrode element 20 by a spacer 16. Normally, the spacer 16 is affixed to the reference electrode element 10 during fabrication, but shown separate from the reference electrode element 10 in FIG. 1A. A cutout portion 13 in the spacer 16 is situated between the reference electrode element 10 and the working element electrode 20, forming a capillary space 17. A first cutout portion 22 in the working electrode element 20 exposes a working electrode area, which is exposed to the capillary space 17. When being affixed to the reference electrode element 10, a first cutout portion 13 in the spacer 16 defines a reference electrode area 14, shown in phantom lines in FIG. 1, which is also exposed to the capillary space 17. Second cutout portions 12 and 23 expose a reference electrode area 11 and a working electrode area 21 respectively, serving as contact pads through which an electrochemical biosensor test strip 30, a meter and a power source are connected to one another.

In an assembled state as shown in FIG. 1B, the electrochemical biosensor test strip 30 has a first opening 32 at its one edge. Further, a vent port 24 in the working electrode element 20 may be incident to a vent port 15 in the reference electrode element 10 so as to provide a second opening 32. In use, a sample containing an analyte may be introduced into the capillary space 17 via either the opening 31 or 32. In either case, the sample is spontaneously drawn into the electrochemical biosensor test strip by capillary action. As a result, the electrochemical biosensor test strip automatically controls the sample volume measured without user intervention.

However, preexisting commercially available electrochemical biosensor test strips, including those described in the patent references supra, suffer from a serious problem as follows: because electrodes are planarity fabricated on substrates and reagents, including enzymes, are immobilized on the electrodes, liquid phases of the reagents are feasible to flow down during the immobilization, so that they are very difficult to immobilize in certain forms. This is highly problematic in terms of the accuracy of detection or measurement because there is a possibility that the reagent immobilized on the electrodes might be different from one to another every test strip. In addition, the electrode area exposed to the capillary space is limitedly formed in the planar substrates which the electrodes occupy. In fact, a narrower electrode area is restricted in detection accuracy.

U.S. Pat. No. 5,437,999 also describes methods for the fabrication of electrodes for electrochemical biosensor test strips, teaching a technique of patterning an electrically conducting material affixed onto an insulating substrate by use of photolithography and a technique of screen printing an electrically conducting material directly onto a standard printed circuit board substrate.

Photolithography, however, usually incurs high production cost. In addition, this technique finds difficulty in mass production because it is not highly successful in achieving fine patterns on a large area.

As for the screen printing, it requires a liquid phase of an electrically conducting material. Although suitable as electrically conducting materials for electrodes by virtue of their superiority in detection performance and chemical resistance, liquid phases of noble metals, such gold, palladium, platinum and the like, are very expensive. Instead of these expensive noble metals, carbon is accordingly employed in practice. The electrode strip obtained by the screen printing of carbon is so significant uneven in its surface that its detection performance is low.

There is also suggested a method for fabricating an electrode for an electrochemical biosensor test strip, in which a thick wire, obtained by depositing palladium onto copper, is bonded on a substrate such as plastic film by heating. This method, however, suffers from a disadvantage in that it is difficult for the electrode strip to be of a narrow, thin shape owing to its procedural characteristics. As the electric charges generated by the reaction between reagents and samples are nearer to the electrodes, they are more probable to be captured and detected by the electrodes. Hence, the bonding of a thick wire onto a plastic film brings about a decrease in the detection efficiency of the electrochemical biosensor test strip. Further, detachment easily occurs between the thick wire and the plastic film owing to a weak bonding strength therebetween and the thick electrode requires high material cost.

SUMMARY OF THE INVENTION

Therefore, it is an object of the present invention to provide an electrochemical biosensor test strip which can firmly fix appropriate reagents in a certain pattern and secure a maximal effective area of an electrode to detect charges, thereby enabling the precise quantitative determination of analytes of interest.

It is another object of the present invention to provide a method for fabricating such an electrochemical biosensor test strip, which is economically favorable as well as gives contribution to the precise detection of analytes by forming an electrode of a uniform surface.

In accordance with an embodiment of the present invention, there is provided an electrochemical biosensor test strip, comprising a first insulating substrate having a groove in a widthwise direction; a pair of electrodes parallel in a lengthwise direction on the first insulating substrate; a reagent for reacting with an analyte of interest to generate a current corresponding to the concentration of the analyte, the reagent being fixed in the groove of the first insulating substrate; and a second insulating substrate bonded onto the first insulating substrate, the second insulating substrate forming a capillary space, along with the groove.

In accordance with another embodiment of the present invention, there is provided a method for fabricating an electrochemical biosensor test strip, comprising the steps of: forming a groove in a first insulating substrate in a widthwise direction; sputtering a metal material onto the first insulating substrate with the aid of a shadow mask to form a pair of electrodes parallel in a lengthwise direction on the first insulating substrate; fixing a reagent within the groove of the first insulating substrate across a pair of the electrodes, the reagent reacting with an analyte of interest to generate a current corresponding to the concentration of the analyte; and bonding a second insulating substrate onto the first insulating substrate, the second insulating substrate forming a capillary space, along with the groove in which the reagent is fixed.

In accordance with a further embodiment of the present invention, there is provided a method for fabricating an electrochemical biosensor test strip, comprising the steps of: sputtering a metal material onto a first insulating substrate with the aid of a shadow mask to form a pair of electrodes parallel in a lengthwise direction on the first insulating substrate; fixing a reagent on the first insulating substrate across a pair of the electrodes, the reagent reacting with an analyte of interest to generate a current corresponding to the concentration of the analyte; and bonding a second insulating substrate having a groove in a widthwise direction onto the first insulating substrate, the groove being positioned across the electrodes and forming a capillary space, along with the groove, at an area corresponding to the reagent fixed.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1A:
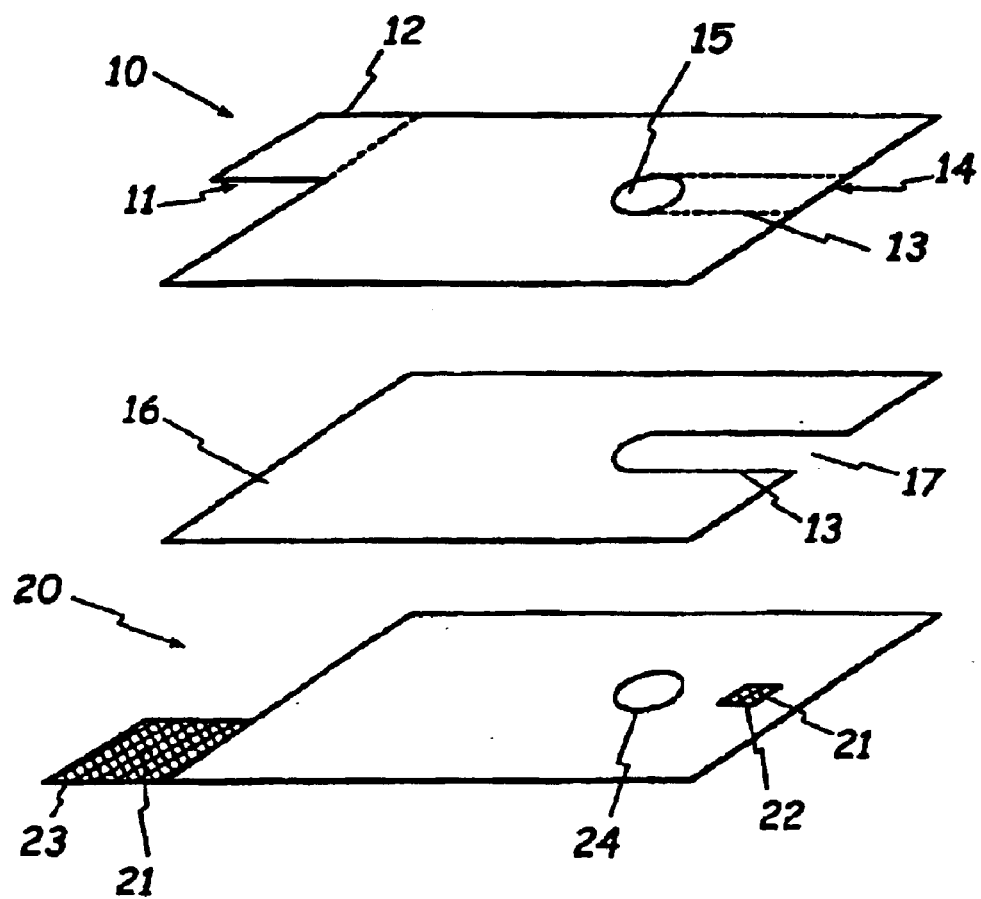
FIG. 1 shows an opposing electrode type of a conventional electrochemical biosensor test strip, specified by a disassembled state in an exploded perspective view of FIG. 1A and by an assembled state in a perspective view of FIG. 1B.
Figure 1B:
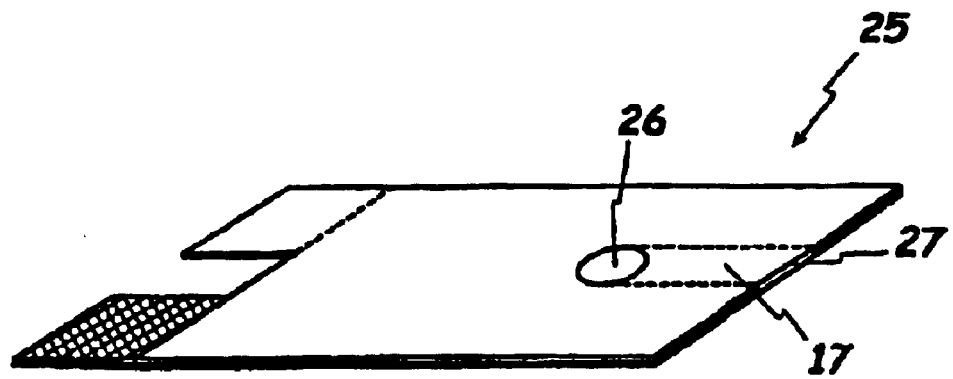

The application of the preferred embodiments of the present invention is best understood with reference to the accompanying drawings, wherein like reference numerals are used for like and corresponding parts, respectively. The preferred embodiments are set forth to illustrate, but are not to be construed to limit the present invention.

Figure 2A:
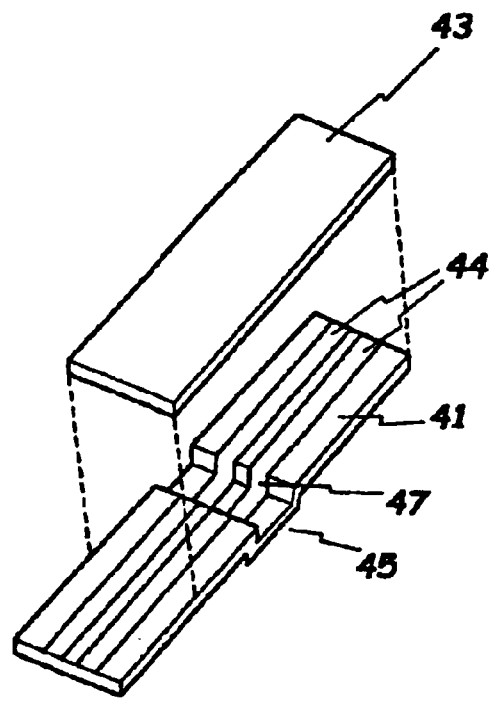
FIG. 2 schematically shows a structure of an electrochemical biosensor test strip according to the present invention in perspective views.
Figure 2B:
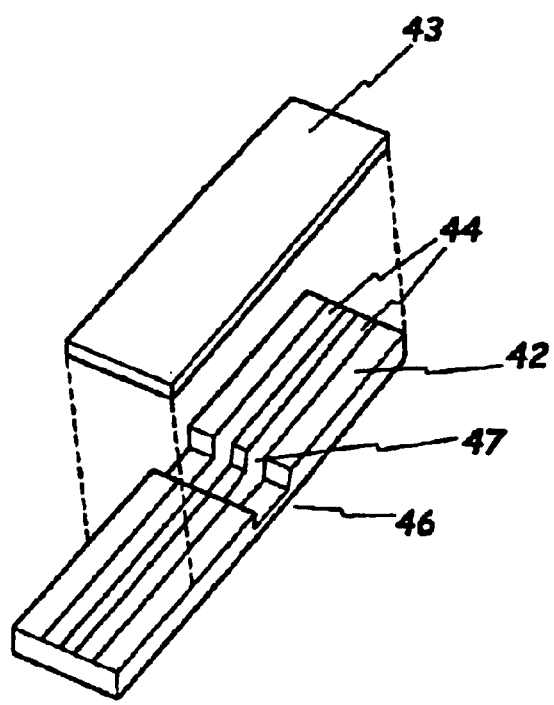

With reference to FIG. 2, there is schematically shown a structure of an electrochemical biosensor test strip according to the present invention in perspective views. As seen, the electrochemical biosensor test strip of the present invention comprising an insulating substrate 41 or 42 on which a groove 45 or 46 is formed by embossing with a pressing or a vacuum molding technique (FIG. 2A) or by engraving (FIG. 2B). An electrode 44 is installed on the insulating substrate 41 or 42. The groove 45 or 46, whether embossed or engraved, has a function of making sure of the fixation of appropriate reagents (not shown) thereonto.

In such a structure of the electrochemical biosensor test strip according to the present invention, therefore, the reagents do not flow over the substrate 41 or 42 while being fixed onto the groove 45 or 46. In other words, the electrochemical biosensor test strip shown in FIG. 2 allows reagents to be immobilized in a certain pattern, thereby making them constant enough to precisely detect or measure analytes of interest.

In addition, as shown in FIG. 2, the electrode installed in the test strip according to the present invention has a three-dimensional structure, so that the electrode area exposed to a capillary space can be further increased as much as an area corresponding to the groove depth (deviant line). This indicates an increase in the electrode area capable of capturing the charges generated by a reagent, resulting in an improvement in detection efficiency.

As illustrated above, the conventional techniques such as screen printing methods and thick-wire bonding methods cannot establish such a precise three-dimensional structure of an electrode in an electrochemical biosensor test strip.

Below, a detail description will be given of a novel method which is able to establish such a precise three-dimensionally structural electrode in an electrochemical biosensor test strip, taking advantages over the conventional methods.

With reference to FIG. 3, there is illustrated a method for fabricating an electrochemical biosensor test strip in accordance with a first embodiment of the present invention.

First, two metal electrode strips 52 and 54 are, in parallel, formed on an insulating substrate 50, one metal electrode strip offering a site of oxidation as a working electrode 52, the other metal electrode strip serving as a corresponding reference electrode 54.

For use in the insulating substrate 50, any material is possible if they are of an electrically insulating property, but in order to produce the electrochemical biosensor test strip of the present invention on mass production, preferable are those which possess flexibility large enough to overcome roll processing as well as sufficient rigidity to be required for supports. Suggested as such insulating substrate materials are polymers, examples of which include polyester, polycarbonate, polystyrene, polyimide, polyvinyl chloride, polyethylene with preference to polyethylene terephthalate.

The formation of the electrode strips 52 and 54 on the insulating substrate 50 is achieved by a sputtering technique with the aid of a shadow mask. In detail after a shadow mask in which an electrode strip contour is patterned is arranged on the insulating substrate 50, a typical sputtering process is conducted, and removal of the shadow mask leaves the electrode strips 52 and 54 on the insulating substrate 50. In this regard, a pre-treatment, such as arc discharging or plasma etching, over the insulating substrate brings about an improvement in the bonding strength between the insulating substrate and the electrode strips. In fact, when an electrode is formed of gold (Au) on an arc-treated plastic film, the bonding strength between the electrode and the insulating substrate was found to be almost perfect (100%) as measured by a taping test.

Figure 4:
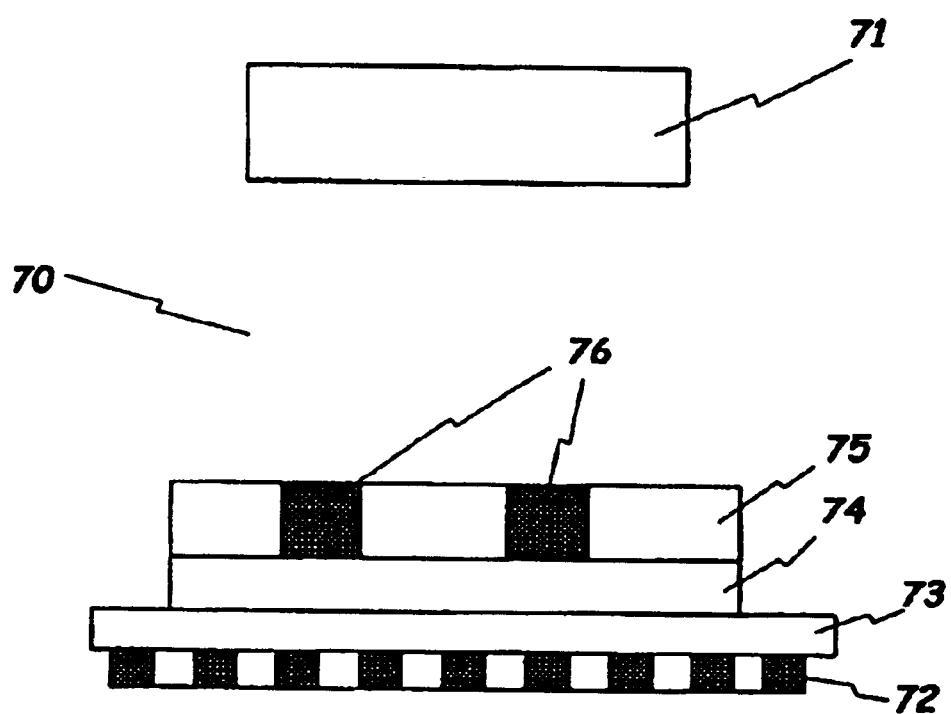
FIG. 4 is a schematic illustration of an process room in which electrodes of a test strip are fabricated by sputtering with the aid of a shadow mask, in accordance with the present invention.

Referring to FIG. 4, there is shown an process room in which a test strip is formed by sputtering with the help of a shadow mask. In this figure, a target is designated as reference numeral 71, a plurality of dot magnets as reference numeral 72, an iron plate as reference numeral 73, an insulating substrate as reference numeral 74, a shadow mask as reference numeral 75, and areas in which electrodes are to be formed as reference numeral 76. Upon sputtering, the mask 75 and the substrate 74 must be in close contact with each other. If there exists a gap therebetween, however small it is, the material to be deposited, e.g., gold, penetrates the gap, thereby resulting in a collapsed pattern. In the present invention, a plurality of dot magnets are employed to bring the shadow mask into a close contact with the insulating substrate 74. In this regard, if the shadow mask 75 is thick, it cannot be affixed to the magnets owing to its own mass and distortion. The experimental data obtained by the present inventors show that a preferable thickness of the shadow mask 75 falls into the range of 0.1 to 0.3 mm.

In accordance with the present invention, the magnets are preferably arranged in an inverse dot pattern. That is, the iron plate 73 is placed on the dot magnets 72. In this case, because the distortion of plasma hardly occurs, a great reduction can be brought about in the distance between the substrate 74 and the target 71, giving rise to a great increase in deposition efficiency.

Where plasma is generated, the process room is feasible to be heated to the temperature at which commonly used plastic films are distorted. In this case, therefore, aluminum alloy, which shows high thermal transmission properties and paramagnetic properties, such as SUS 430, is used as the shadow mask.

Suitable for use in electrodes are noble metals. Examples of the noble metals include palladium, platinum, gold, silver and so on by virtue of superior electrochemical properties in terms of stability on electrode surface regions, electrochemical reproductivity, resistance to oxidation, etc. Particularly preferable is gold which enjoys advantages of being relatively inexpensive, simple to process, superb in adhesiveness to plastic, and high in electrical conductivity. Although an electrode is formed of gold at as thin as 100 nm by sputtering, it is suitable as a disposable one because it has an electrically low resistance and is mechanically firmly affixed to an insulating substrate such as a plastic film. Alternatively, rather than such noble metals only, metal materials which are highly adhesive to insulating substrates, such as plastics, and are inexpensive, may be used to form a primary electrode on which the noble metal is thinly covered, for an economical reason.

Returning to FIG. 3B, a reagent 56 reactive to analytes is affixed with a suitable width across the two electrodes 52 and 54 on the insulating substrate 50. The electrochemical biosensor test strip of the present invention can target a broad spectrum of analytes. Body materials, such as whole blood, blood serum, urine, neurotransmitters and the like, as well as fermented or naturally occurring materials can be detected or measured by the electrochemical biosensor test strip of the present invention. The reagent 56 can be coated on the electrode area of the insulating substrate 50 with the aid of an automatic dispenser or by use of a screen printing, a roll coating, or a spin coating technique. When an electric potential is applied across the two electrodes after a sample is provided, the reagent reacts with the sample in a reaction time period to generate charges. Because these charges, which are generated through enzymatic reactions, relates to the concentration of the analyte of interest, the quantitative determination of the charges provides knowledge in regard to the concentration of the analyte.

Available as the reagent 56 are enzymes or redox mediators. A variety of enzymes can be used in dependence on the analytes to be detected or measured. For example, when glucose is to be detected or analyzed, glucose oxidase may be used. Useful redox mediators may be exemplified by potassium ferricyanide and an imidazole osmium mediator which is disclosed in U.S. Pat. No. 5,437,999. Besides enzymes and redox mediators, the reagent 56 may further comprise buffers, hydrophilic macromolecules, surfactants, and/or film-forming agents. During the reaction with a sample, a buffer in the reagent functions to keep a pH condition constant. On the other hand, the hydrophilic macromolecules are useful to fix other reagent components onto the electrode. Meanwhile, surfactants facilitate the introduction of samples into a capillary space, which will be explained later, by capillary action. Thus, the reagent for the detection or measurement of glucose may comprise potassium ferricyanide, a potassium phosphate buffer, cellulose, hydroxyethyl cellulose, a Triton X-100 surfactant, sodium succinate, and glucose oxidase in combination. A detailed preparation method of such reagents, and available enzymes and redox mediators can be referred to U.S. Pat. No. 5,762,770.

Figure 3A:
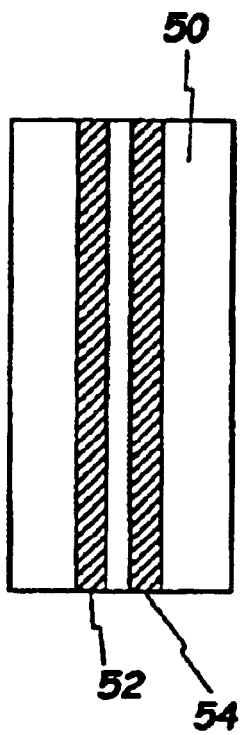
FIG. 3 shows a process for fabricating a test strip in accordance with a first embodiment of the present invention.
Figure 3B:
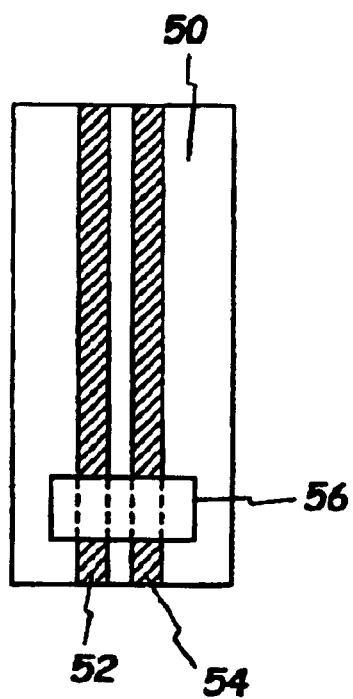
Figure 3C:
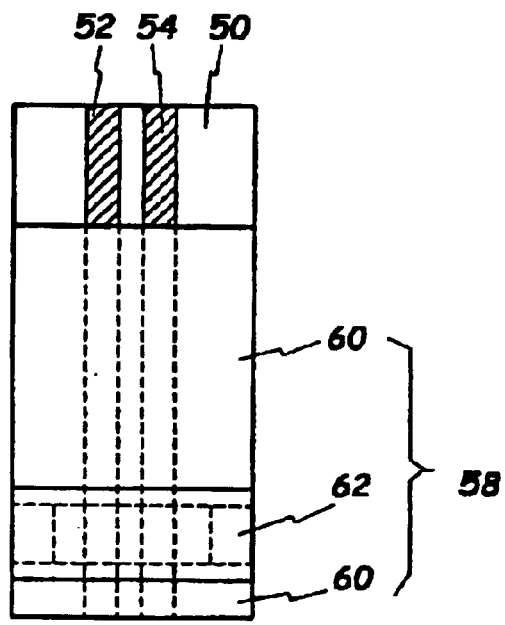
Figure 3D:
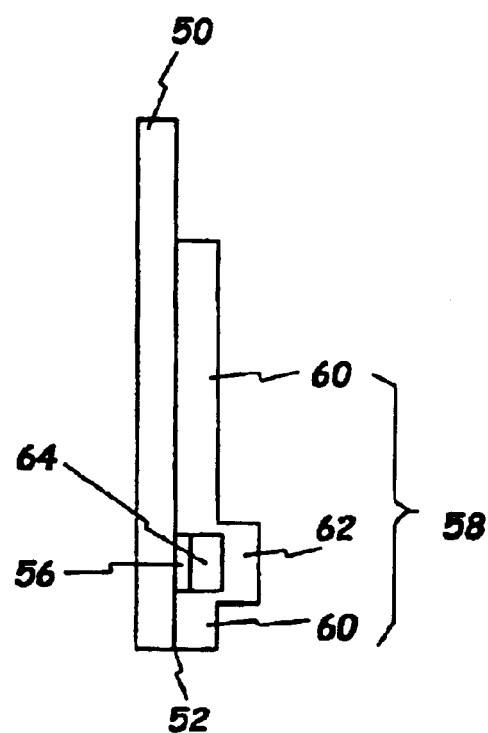

With reference to FIG. 3C, an insulating plate 58 is fixed onto the electrodes 52 and 54 and the insulating substrate by thermocompression bonding or via a double-sided adhesive. FIG. 3D shows a profile of the structure of FIG. 3C. As seen, the insulating plate 58 has a region to be in contact with the electrodes 52 and 54 and the insulating substrate 50 and a protruded region corresponding to the area onto which the reagent 56 is affixed. Suitable as a material for use in the insulating plate 58 may be the same as the material for the insulating substrate 50. Without being covered by the insulating plate 58, an upper part of the insulating substrate 50 remains bared. The electrodes 52 and 54, which are partially exposed at their upper parts, can serve as contact pads through which the electrochemical biosensor test strip, a meter and a power source are electrically connected to one another.

As shown in FIG. 3D, the protruded region of the insulating plate 58, along with the insulating substrate 50, forms a capillary space 64 which transverses the electrodes 52 and 54 in a widthwise direction. The capillary space needs not be completely as wide as, but may be wider or narrower than the reagent 56. Likewise, the length of the capillary space also needs not be completely the same as, but may be greater or smaller than the width of the insulating substrate 50. Only in order to reduce the error which occurs upon the introduction of a sample into the capillary space, the length of the capillary space preferably agrees with the width of the insulating substrate 50. The capillary space 64 thus formed is where a sample such as blood is introduced. This introduction is facilitated by a capillary action such that a precise determination can be done with even a small quantity of a sample.

Following is the principle of measuring the concentration of an analyte of interest, that is, a matter to be detected and/or analyzed, by use of the electrochemical biosensor test strip of the present invention. When a glucose level in blood is assayed by use of a glucose oxidase with potassium ferricyanide as a redox mediator, for instance, the glucose is oxidized while the ferricyanide is reduced into ferrocyanide, both being catalyzed by the glucose oxidase. After a predetermined period of time, when an electrical potential from a power source is applied across the two electrodes, a current is passed by the electron transfer attributed to the re-oxidation of the ferrocyanide. The electrical potential applied across the two electrodes from a power source is suitably not more than 300 mV and preferably on the order of around 100 mV when taking the properties of the mediator into account.

By applying a stored algorithm to the current meter, the current thus measured can be revealed as a dependent variable relative to the concentration of the analyte in the sample. In another mathematical method, by integrating the current measured in a current-time curve against a certain period of time, the total quantity of charges generated during the time period can be obtained, which is directly proportional to the concentration of the analyte. In brief the concentration of an analyte in a sample can be quantitatively determined by measuring the diffusing current which is generated by the enzymatic reaction-based electrical oxidation of a redox mediator.

Now, turning to FIG. 5, there are stepwise illustrated processes of fabricating electrodes by sputtering with the aid of a adhesive-type shadow mask.

Figure 5A:
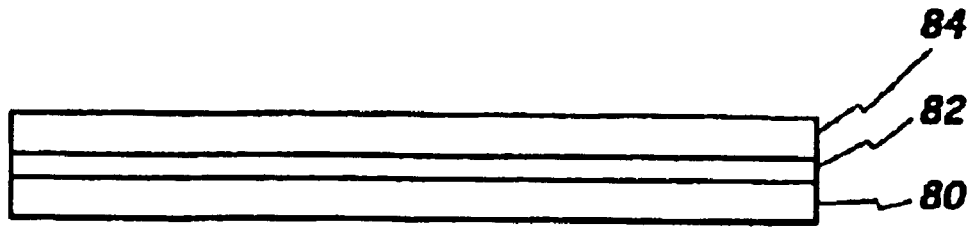
FIG. 5 shows a sputtering process with the aid of an adhesive-type shadow mask in schematic cross sectional views.

A plastic film 80 is provided onto which a plastic film 84 as a shadow mask is attached via an adhesive layer 82, as shown in FIG. 5A. The adhesive layer 82 is in an interim attachment state to the plastic film 80, so they can be easily detached from each other.

Figure 5B:
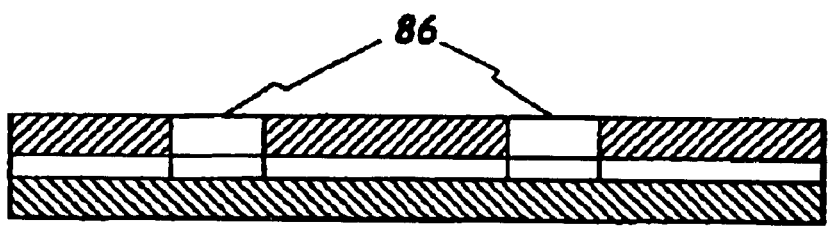

Next, the plastic film 84 and the adhesive layer 82 are cut at predetermined regions in the pattern of the electrodes to be formed, with the aid of a cutting plotter or an engraver, as shown in FIG. 5B.

Figure 5C:
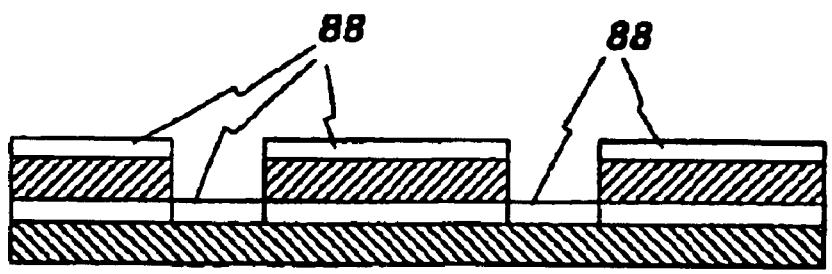

Subsequently, the cut regions are taken off, followed by vacuum sputtering gold 88 wholly over the remaining structure to form electrodes with the plastic film 84 being used as a shadow mask, as shown in FIG. 5C.

Figure 5D:
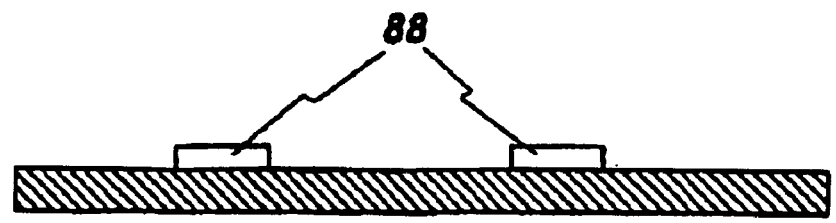

Finally, the remaining plastic film 84 and adhesive layer 82 are removed to bare the electrodes, as shown in FIG. 5D.

Like this case, an adhesive-type shadow mask allows patterns to be formed to the extent of the processing limit of a cutting plotter. Also, in contrast to typical iron shadow masks, such an adhesive-type shadow mask is flexible and attached to the film on which electrodes are to be formed, so that precise patterns can be established by sputtering without lateral diffusion.

Referring to FIG. 6, the method according to the present invention is applied for the fabrication of an electrochemical biosensor test strip.

Figure 6A:
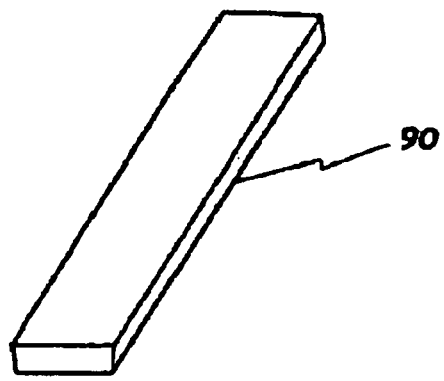
FIG. 6 shows a process for fabricating a test strip in accordance with a second embodiment of the present invention.

First, there is provided a plastic substrate 90 on which a structure of an electrode strip is to be constructed, as shown in FIG. 6A.

Figure 6B:
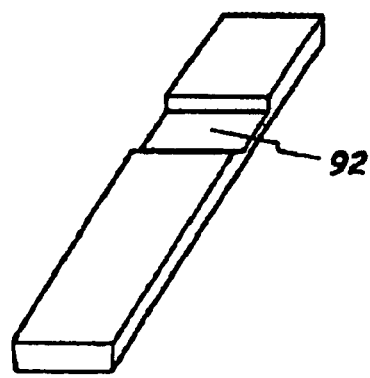

Thereafter, a groove 92 is formed in a widthwise direction on the plastic substrate 92, as shown in FIG. 6B. In this regard, it is preferred that both side banks 93 of the groove are slightly slanted lest gold electrodes, as will be deposited later, should be cut at their edges. For the formation of the groove 92, a pressing or a vacuum molding method may be used to emboss the surface of the plastic substrate 90. Alternatively, the groove 92 can be formed by use of an engraver. The latter method is adapted to form the groove 92 of FIG. 6B. Since the matter for the plastic film 90 is usually wound around a roll, an engraver is more preferably used to groove the plastim film in light of mass production. This procedure enables only two sheets of plastic film to be formed into an electrochemical biosensor test strip which has a capillary space built-in, without additionally using a spacer as in U.S. Pat. No. 5,437,999.

Figure 6C:
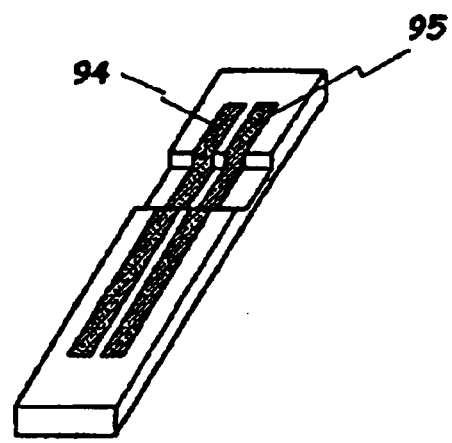
Figure 6D:
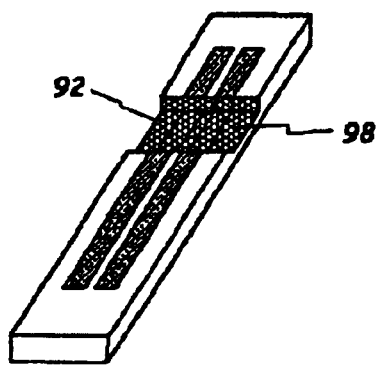

Afterwards, electrode strips 94 and 95 are formed, as shown in FIG. 6C. For this, gold is vacuum sputtered onto the plastic substrate 90 with the aid of a shadow mask, as previously mentioned. A reagent 98 is coated within the groove 92 across the working electrode and the reference electrode and dried, as shown in FIG. 6D.

For the purpose of establishing such a three-dimensional structure of an electrode strip as shown in FIG. 6C, the adoption of a planar shadow mask onto the grooved substrate makes a gap as high as the capillary tube between the mask and the substrate, through which gold from the target 71 penetrates, resulting in the formation of dull-defined patterns. To avoid this problem, the following three techniques are employed. First, the shadow mask is constructed so crookedly that it fits to the groove shape. By virtue of superb processability, SUS 430 can be formed into such a three-dimensional structure of the shadow mask. Another solution is to control process parameters or the structure of the process room. The lower the pressure of the process room, the longer the mean free path of the gold atoms sputtered. Thus, the atoms incident in the perpendicular direction onto the substrate become dense in number. In other words, fewer atoms run in the lateral direction, resulting in the more precise definition of electrodes. In addition, lengthening the distance between the target 71 and the substrate 74 makes a net flux of sputtered atoms perpendicular to the substrate 74. Where a five-inch circular target is employed, for example, almost no spread patterning is found if the distance from the substrate is over 7 cm. The last measure the present invention takes to overcome the dull definition of electrode patterns is use of a collimator to block the atoms from running in a lateral direction. In contrast to a honeystructure of collimators, usually used in semiconductor processes, the collimator used in the present invention is of a blind pattern because it can restrict the running of atoms only in a lateral direction.

Figure 6E:
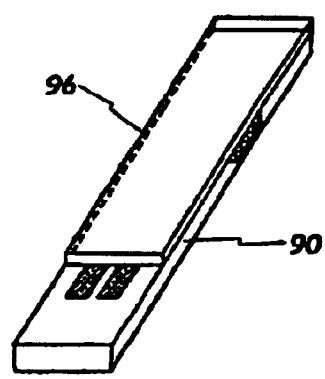
Figure 6F:
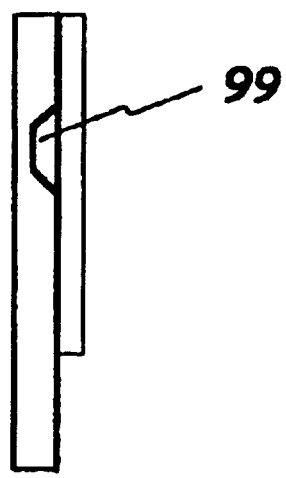

Finally, an insulating plate 96 is bonded onto the plastic substrate 90 in such a way that a major portion of the plastic substrate 90, including the groove 92, is covered with the insulating plate 96 while the other upper part remains uncovered, as shown in FIG. 6E. In result, the groove forms a capillary space, along with the insulating plate 96. Through the capillary space, a sample such as blood is introduced into the electrochemical biosensor test strip. A profile of the finished electrochemical biosensor test strip of FIG. 6E is shown in FIG. 6F with an exaggerated illustration of the capillary space 99.

INDUSTRIAL APPLICABILITY

As described hereinbefore, the test strip of the present invention is capable of precise quantitative determination of analytes of interest by virtue of its firm fixation of appropriate reagents in a certain pattern and of its possessing of a maximal effective area of an electrode to detect charges.

In addition, the method for fabricating such a test strip according to the present invention thin electrode is economically favorable owing to use of the thin electrode films and gives contribution to the precise detection of analytes by forming an electrode of a uniform surface from gold, which is chemically stable.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. An electrochemical biosensor test strip, comprising:
   a first insulating substrate having a groove in a widthwise direction;
   a pair of electrodes parallel in a lengthwise direction across the groove on the first insulating substrate;
   a reagent for reacting with an analyst of interest to generate a current corresponding to the concentration of the analyte, the reagent being fixed in the groove of the fist insulating substrate; and
   a second insulating substrate bonded into the first insulating substrate, the second insulating substrate forming a capillary space, along with the groove.

2. The electrochemical biosensor test strip as set forth in claim 1, wherein the electrodes are formed of a noble metal selected from the group consisting of gold, silver, platinum and palladium.

3. The electrochemical biosensor test stop as set forth in claim 1, wherein the electrodes are formed of a double layer structure comprising a lower layer of a metal and an upper layer of a noble metal select from the group consisting of gold, silver, platinum and palladium.

4. The electrochemical biosensor test strip as set forth in claim 1, wherein the first insulating substrate is formed of a polymer selected from the group consisting of polyethylene terephthalate, polyester, polycarbonate, polystyrene, polyimide, polyvinyl chloride, and polyethylene.

5. A biosensor system, comprising:
   an electrochemical biosensor test stop of claim 1; and
   a detector for displaying an analyte concentration in a sample, the detector being electrically connected with both the working electrode and the reference electrode, applying an electric potential across the two electrodes, and measuring the current generated as a result of the reaction between the reagent and the sample.

6. A method for fabricating an electrochemical biosensor test strip, comprising the steps of:
   forming a groove in a first insulating substrate in a widthwise direction;
   sputtering a metal material onto the first insulating substrate with the aid of a shadow mask to form a pair of electrodes parallel in a longwise direction across the groove on the first insulating substrate;
   fixing a reagent within the groove of the first insulating substrate across a pair of the electrodes, the reagent reacting with an analyte of interest to generate a current corresponding to the concentration of the analyte; and
   bonding a second insulating substrate onto the first insulating substrate, the second insulating substrate forming a capillary space, along with the groove in which the reagent is fixed.

7. The method as set forth in claim 6, wherein the electrodes are formed of a noble metal selected from the group consisting of gold, silver, platinum and palladium.

8. The method as set forth in claim 6, wherein the electrodes are formed of a double layer structure comprising a lower layer of a metal and an upper layer of a noble metal selected from the group consisting of gold, silver, platinum and palladium.

9. The method as set forth in claim 6, wherein the shadow mask is attached to the first insulating substrate by sue of a magnet.

10. The method as set forth in claim 6, wherein the shadow mask is formed of an aluminum alloy which is excellent in thermal transmission and magnetic properties.

11. The method as set forth in claim 6, wherein the shadow mask ranges, in thickness, from 0.1 to 0.3 mm.

12. The method as set forth in claim 6, wherein the sputtering step comprises:
    applying an adhesive layer over the first insulating substrate to bond a mask film onto the first insulating substrate;
    cutting the mask film and adhesive in a desired pattern;
    removing the cut area from the mask film and adhesive and depositing a metal element over the resulting structure; and
    removing the remaining mask film and adhesive.

13. The method as set forth in claim 6, wherein the fist insulating substrate is formed of a polymer selected from the group consisting of polyethylene terephthalate, polyester, polycarbonate, polystyrene, polyimide, polyvinyl chloride, and polyethylene.

14. The method as set forth in claim 6, further comprising the step for conducting an arc discharging or a plasma etching process over the first insulating substrate, prior to the sputtering step.

15. The method as set forth in claim 6, wherein the shadow mask has a three-dimensional structure suitable to fit to the groove of the first insulating substrate.

16. The method as set forth in claim 6, wherein the sputtering step is conducted using a collimater.

\* \* \* \* \*